US00RE47470E

(19) United States
(12) Reissued Patent
Hovda et al.

(10) Patent Number: US RE47,470 E
(45) Date of Reissued Patent: Jul. 2, 2019

(54) VERTEBRAL BODY PLACEMENT AND METHOD FOR SPANNING A SPACE FORMED UPON REMOVAL OF A VERTEBRAL BODY

(71) Applicant: Simplify Medical Pty Ltd, Paddington (AU)

(72) Inventors: David Hovda, Mountain View, CA (US); Yves Arramon, Sunnyvale, CA (US)

(73) Assignee: Simplify Medical Pty Ltd (AU)

(21) Appl. No.: 15/191,385

(22) Filed: Jun. 23, 2016

Related U.S. Patent Documents

Reissue of:
(64) Patent No.: 8,758,441
Issued: Jun. 24, 2014
Appl. No.: 12/255,737
Filed: Oct. 22, 2008

U.S. Applications:
(60) Provisional application No. 60/981,665, filed on Oct. 22, 2007.

(51) Int. Cl.
*A61F 2/44* (2006.01)
*A61F 2/30* (2006.01)
*A61B 17/86* (2006.01)

(52) U.S. Cl.
CPC ..... *A61F 2/30771* (2013.01); *A61F 2/4465* (2013.01); *A61B 17/86* (2013.01);
(Continued)

(58) Field of Classification Search
None
See application file for complete search history.

(56) References Cited

U.S. PATENT DOCUMENTS 3,867,728 A 2/1975 Stubstad et al.
4,309,777 A 1/1982 Patil
(Continued)

FOREIGN PATENT DOCUMENTS

DE 3023353 A1 4/1981
DE 3023353 A1 4/1981
(Continued)

OTHER PUBLICATIONS

Chadwick et al., Radiolucent Structural Materials for Medical Applications, Jun. 1, 2001, MDDI, p. 1, http://www.mddionline.com/article/radiolucent-structural-materials-medical-applications.*
(Continued)

*Primary Examiner* — Cary E Wehner
(74) *Attorney, Agent, or Firm* — Wilson Sonsini Goodrich & Rosati

(57) ABSTRACT

A vertebral body replacement includes first and second end plates, and a compliant connector section between the end plates having one or more helical cuts to provide limited compliance between the end plates. The compliant connector section can be provided in a separate spacer that fits between the end plates or directly in one or more of the end plates. The adjoining end plate surfaces, and/or adjoining surfaces of the spacer, include a rotational interlock to inhibit rotational motion between the surfaces and allow a modular stacking assembly of the vertebral body replacement to accommodate a wide range of patients.

27 Claims, 4 Drawing Sheets

(52) U.S. Cl.
CPC ..... *A61F 2002/30056* (2013.01); *A61F 2002/30772* (2013.01); *A61F 2002/30787* (2013.01); *A61F 2002/30884* (2013.01); *A61F 2002/30889* (2013.01); *A61F 2002/30904* (2013.01); *A61F 2002/449* (2013.01); *A61F 2250/0032* (2013.01); *A61F 2310/0088* (2013.01); *A61F 2310/00407* (2013.01); *A61F 2310/00431* (2013.01); *A61F 2310/00604* (2013.01); *A61F 2310/00796* (2013.01); *A61F 2310/00976* (2013.01)

(56) References Cited

U.S. PATENT DOCUMENTS 4,531,917 A 7/1985 Linkow et al.
4,566,466 A 1/1986 Ripple et al.
4,619,660 A 10/1986 Christiansen et al.
4,673,407 A 6/1987 Martin
4,759,766 A 7/1988 Buttner-Janz et al.
4,759,769 A 7/1988 Hedman et al.
4,834,757 A 5/1989 Brantigan
4,863,477 A 9/1989 Monson
4,904,261 A 2/1990 Dove et al.
4,917,704 A 4/1990 Frey et al.
4,932,969 A 6/1990 Frey et al.
4,946,378 A 8/1990 Hirayama et al.
4,997,432 A * 3/1991 Keller ..... 623/17.11
5,035,716 A 7/1991 Downey
5,057,108 A 10/1991 Shetty et al.
5,071,437 A 12/1991 Steffee
5,122,130 A 6/1992 Keller
5,192,327 A * 3/1993 Brantigan ..... 623/17.11
5,195,526 A 3/1993 Michelson
5,258,031 A 11/1993 Salib et al.
5,282,861 A 2/1994 Kaplan
5,306,308 A 4/1994 Gross et al.
5,314,477 A 5/1994 Marnay
5,320,644 A 6/1994 Baumgartner
5,370,697 A 12/1994 Baumgartner
5,394,457 A 2/1995 Leibinger et al.
5,401,269 A 3/1995 Buttner-Janz et al.
5,415,704 A 5/1995 Davidson
5,423,816 A * 6/1995 Lin ..... 606/247
5,458,642 A 10/1995 Beer et al.
5,462,575 A 10/1995 Del Corso
5,484,437 A 1/1996 Michelson
5,489,307 A 2/1996 Kuslich et al.
5,505,732 A 4/1996 Michelson
5,507,816 A 4/1996 Bullivant
5,534,030 A 7/1996 Navarro et al.
5,556,431 A 9/1996 Buttner-Janz
5,674,296 A 10/1997 Bryan et al.
5,676,701 A 10/1997 Yuan et al.
5,676,702 A 10/1997 Ratron
5,683,465 A 11/1997 Shinn et al.
5,702,450 A 12/1997 Bisserie
5,709,683 A 1/1998 Bagby
5,728,159 A 3/1998 Stroever et al.
5,741,253 A 4/1998 Michelson
5,776,198 A 7/1998 Rabbe et al.
5,782,832 A 7/1998 Larsen et al.
5,797,909 A 8/1998 Michelson
5,797,917 A * 8/1998 Boyd et al. ..... 606/99
5,824,094 A 10/1998 Serhan et al.
5,836,948 A 11/1998 Zucherman et al.
5,865,846 A 2/1999 Bryan et al.
5,865,848 A 2/1999 Baker
5,888,226 A 3/1999 Rogozinski
5,895,428 A 4/1999 Berry
5,899,901 A 5/1999 Middleton
5,899,911 A 5/1999 Carter
5,928,284 A 7/1999 Mehdizadeh
5,989,251 A 11/1999 Nichols
5,989,291 A 11/1999 Ralph et al.
6,001,130 A 12/1999 Bryan et al.
6,019,792 A 2/2000 Cauthen
6,022,376 A 2/2000 Assell et al.
6,039,761 A 3/2000 Li et al.
6,039,763 A 3/2000 Shelokov
6,080,155 A 6/2000 Michelson
6,083,228 A 7/2000 Michelson
6,086,613 A 7/2000 Camino et al.
6,096,038 A 8/2000 Michelson
6,106,557 A * 8/2000 Robioneck et al. ..... 623/17.15
6,132,465 A 10/2000 Ray et al.
6,136,031 A 10/2000 Middleton
6,139,551 A 10/2000 Michelson et al.
6,139,579 A 10/2000 Steffee et al.
6,143,033 A 11/2000 Paul et al.
6,146,421 A 11/2000 Gordon et al.
6,156,067 A 12/2000 Bryan et al.
6,159,211 A * 12/2000 Boriani et al. ..... 606/279
6,159,214 A 12/2000 Michelson
6,162,252 A 12/2000 Kuras et al.
6,174,311 B1 1/2001 Branch et al.
6,176,881 B1 1/2001 Schar et al.
6,193,757 B1 2/2001 Foley et al.
6,224,595 B1 5/2001 Michelson
6,224,607 B1 5/2001 Michelson
6,231,609 B1 5/2001 Mehdizadeh
6,235,030 B1 5/2001 Zucherman et al.
6,261,296 B1 7/2001 Aebi et al.
6,264,695 B1 7/2001 Stoy
6,290,726 B1 9/2001 Pope et al.
6,296,664 B1 10/2001 Middleton
6,315,797 B1 * 11/2001 Middleton ..... 623/17.16
6,322,567 B1 11/2001 Mittelstadt et al.
6,336,941 B1 1/2002 Subba Rao et al.
6,348,071 B1 2/2002 Steffee et al.
6,368,350 B1 4/2002 Erickson et al.
6,368,351 B1 4/2002 Glenn et al.
6,375,681 B1 4/2002 Truscott
6,375,682 B1 4/2002 Fleischmann et al.
6,395,032 B1 5/2002 Gauchet
6,402,785 B1 6/2002 Zdeblick et al.
6,409,766 B1 6/2002 Brett
6,413,278 B1 7/2002 Marchosky
6,416,551 B1 7/2002 Keller
6,436,098 B1 8/2002 Michelson
6,440,139 B2 8/2002 Michelson
6,447,544 B1 9/2002 Michelson
6,478,800 B1 11/2002 Fraser et al.
6,517,544 B1 2/2003 Michelson
6,517,580 B1 2/2003 Ramadan et al.
6,520,967 B1 2/2003 Cauthen
6,520,996 B1 2/2003 Manasas et al.
6,527,804 B1 3/2003 Gauchet et al.
6,533,817 B1 3/2003 Norton et al.
6,537,279 B1 3/2003 Michelson
6,554,863 B2 4/2003 Paul et al.
6,562,047 B2 5/2003 Ralph et al.
6,562,074 B2 5/2003 Gerbec et al.
6,565,574 B2 5/2003 Michelson
6,579,321 B1 6/2003 Gordon et al.
6,582,466 B1 6/2003 Gauchet
6,582,468 B1 6/2003 Gauchet
6,592,624 B1 7/2003 Fraser et al.
6,599,294 B2 7/2003 Fuss et al.
6,607,558 B2 8/2003 Kuras
6,607,559 B2 8/2003 Ralph et al.
6,610,092 B2 8/2003 Ralph et al.
6,623,525 B2 9/2003 Ralph et al.
6,645,248 B2 11/2003 Casutt
6,648,895 B2 11/2003 Burkus et al.
6,652,533 B2 11/2003 O'Neil
6,660,038 B2 12/2003 Boyer, II et al.
6,666,866 B2 12/2003 Martz et al.
6,669,731 B2 12/2003 Ralph et al.
6,669,732 B2 12/2003 Serhan et al.
6,673,113 B2 1/2004 Ralph et al.
6,682,562 B2 1/2004 Viart et al.
6,689,132 B2 2/2004 Biscup
6,706,068 B2 3/2004 Ferree

(56) References Cited

U.S. PATENT DOCUMENTS 6,709,439 B2 3/2004 Rogers et al.
6,712,819 B2 3/2004 Zucherman et al.
6,712,825 B2 3/2004 Aebi et al.
6,719,794 B2 4/2004 Gerber et al.
6,723,097 B2 4/2004 Fraser et al.
6,726,720 B2 4/2004 Ross et al.
6,726,721 B2 4/2004 Stoy et al.
6,733,532 B1 5/2004 Gauchet et al.
6,740,118 B2 5/2004 Eisermann et al.
6,740,119 B2 5/2004 Ralph et al.
6,752,832 B2 6/2004 Neumann
6,755,841 B2 6/2004 Fraser et al.
6,764,512 B2 7/2004 Keller
6,764,515 B2 7/2004 Ralph et al.
6,770,095 B2 8/2004 Grinberg et al.
6,790,233 B2 9/2004 Brodke et al.
6,793,678 B2 9/2004 Hawkins
6,814,737 B2 11/2004 Cauthen
6,821,298 B1 11/2004 Jackson
6,827,740 B1 12/2004 Michelson
6,830,570 B1 12/2004 Frey et al.
6,835,206 B2 12/2004 Jackson
6,846,328 B2 1/2005 Cauthen
6,852,126 B2 2/2005 Ahlgren
6,863,673 B2 3/2005 Gerbec et al.
6,875,213 B2 4/2005 Michelson
6,896,680 B2 5/2005 Michelson
6,899,735 B2 5/2005 Coates et al.
6,936,071 B1 8/2005 Marnay et al.
6,936,132 B2 8/2005 Topolnitsky
6,964,686 B2 11/2005 Gordon ..... A61F 2/442 623/17.14
6,966,929 B2 11/2005 Mitchell
6,966,931 B2 11/2005 Huang
6,986,788 B2 1/2006 Paul et al.
6,989,011 B2 1/2006 Paul et al.
6,994,727 B2 2/2006 Khandkar et al.
7,011,684 B2 3/2006 Eckman
7,022,138 B2 4/2006 Mashburn
7,025,787 B2 4/2006 Bryan et al.
7,044,972 B2 5/2006 Mathys et al.
7,044,983 B1 5/2006 Cheng
7,056,344 B2 6/2006 Huppert et al.
7,060,073 B2 6/2006 Frey et al.
7,066,958 B2 6/2006 Ferree
7,081,120 B2 7/2006 Li et al.
7,083,651 B2 8/2006 Diaz et al.
7,087,055 B2 8/2006 Lim et al.
7,097,648 B1 8/2006 Globerman et al.
7,115,132 B2 10/2006 Errico et al.
7,118,580 B1 10/2006 Beyersdorff et al.
7,147,665 B1 12/2006 Bryan et al.
7,153,325 B2 12/2006 Kim et al.
7,169,182 B2 1/2007 Errico et al.
7,179,294 B2 2/2007 Eisermann et al.
7,182,784 B2 2/2007 Evans et al.
7,198,644 B2 4/2007 Schultz et al.
7,207,991 B2 4/2007 Michelson
7,214,244 B2 5/2007 Zubok et al.
7,217,291 B2 5/2007 Zucherman et al.
7,235,082 B2 6/2007 Bartish et al.
7,235,101 B2 * 6/2007 Berry et al. ..... 623/17.11
7,235,103 B2 6/2007 Rivin
7,250,060 B2 7/2007 Trieu
7,255,714 B2 8/2007 Malek
7,261,739 B2 8/2007 Ralph et al.
7,267,688 B2 9/2007 Ferree
7,270,679 B2 9/2007 Istephanous et al.
7,270,682 B2 9/2007 Frigg et al.
7,303,582 B2 12/2007 Brady
7,303,583 B1 12/2007 Schär et al.
7,309,358 B2 * 12/2007 Berry et al. ..... 623/17.16
7,318,839 B2 1/2008 Malberg et al.
7,326,250 B2 2/2008 Beaurain et al.
7,331,994 B2 * 2/2008 Gordon ..... A61F 2/442 623/17.13
7,331,995 B2 2/2008 Eisermann et al.
7,429,270 B2 9/2008 Baumgartner et al.
7,442,211 B2 10/2008 de Villiers et al.
7,452,380 B2 11/2008 Zubok et al.
7,491,241 B2 2/2009 Errico et al.
7,494,508 B2 2/2009 Zeegers
7,517,363 B2 4/2009 Rogers et al.
7,531,001 B2 5/2009 de Villiers et al.
7,549,995 B2 6/2009 Schultz et al.
7,563,284 B2 7/2009 Coppes et al.
7,563,286 B2 7/2009 Gerber et al.
7,575,598 B2 * 8/2009 Albert et al. ..... 623/17.13
7,578,848 B2 * 8/2009 Albert et al. ..... 623/17.13
7,585,324 B2 * 9/2009 Albert et al. ..... 623/17.13
7,585,326 B2 9/2009 de Villiers et al.
7,615,078 B2 * 11/2009 White et al. ..... 623/17.16
7,635,368 B2 12/2009 Errico et al.
7,637,913 B2 12/2009 de Villiers et al.
7,655,045 B2 2/2010 Richelsoph
7,708,776 B1 5/2010 Blain et al.
7,708,777 B2 5/2010 O'Neil et al.
7,731,753 B2 6/2010 Reo et al.
7,731,754 B2 6/2010 de Villiers et al.
7,749,272 B2 7/2010 Robie et al.
7,763,055 B2 7/2010 Foley
7,819,922 B2 * 10/2010 Sweeney ..... 623/17.16
8,057,545 B2 11/2011 Hughes et al.
8,092,534 B2 1/2012 Eckhardt
8,142,505 B2 3/2012 Tauber
8,298,287 B2 * 10/2012 Moumene ..... A61F 2/442 623/17.16
8,491,637 B2 * 7/2013 Matthis ..... A61B 17/702 606/254
8,758,441 B2 6/2014 Hovda et al.
8,771,357 B2 * 7/2014 Biedermann ..... A61F 2/44 623/17.11
2001/0016773 A1 8/2001 Serhan et al.
2001/0029377 A1 10/2001 Aebi et al.
2001/0051829 A1 12/2001 Middleton
2002/0022845 A1 2/2002 Zdeblick et al.
2002/0035400 A1 3/2002 Bryan et al.
2002/0045904 A1 4/2002 Fuss et al.
2002/0068936 A1 6/2002 Burkus et al.
2002/0091392 A1 7/2002 Michelson
2002/0116009 A1 8/2002 Fraser et al.
2002/0123753 A1 9/2002 Michelson
2002/0128715 A1 9/2002 Bryan et al.
2002/0165550 A1 11/2002 Frey et al.
2002/0177897 A1 11/2002 Michelson
2002/0198532 A1 12/2002 Michelson
2003/0009224 A1 1/2003 Kuras
2003/0014116 A1 1/2003 Ralph et al.
2003/0023245 A1 1/2003 Ralph et al.
2003/0028249 A1 2/2003 Baccelli et al.
2003/0040746 A1 2/2003 Mitchell et al.
2003/0045884 A1 3/2003 Robie et al.
2003/0045939 A1 3/2003 Casutt
2003/0074076 A1 4/2003 Ferree
2003/0083747 A1 5/2003 Winterbottom et al.
2003/0100951 A1 5/2003 Serhan et al.
2003/0125739 A1 7/2003 Bagga
2003/0130662 A1 7/2003 Michelson
2003/0135277 A1 7/2003 Bryan et al.
2003/0139812 A1 7/2003 Garcia et al.
2003/0187448 A1 10/2003 Michelson
2003/0191536 A1 10/2003 Ferree
2003/0195517 A1 10/2003 Michelson
2003/0195631 A1 10/2003 Ferree
2003/0199982 A1 10/2003 Bryan
2003/0199983 A1 * 10/2003 Michelson ..... 623/17.16
2003/0204261 A1 10/2003 Eisermann et al.
2003/0208271 A1 11/2003 Kuras
2003/0229358 A1 12/2003 Errico et al.
2003/0233145 A1 12/2003 Landry et al.
2004/0002761 A1 1/2004 Rogers et al. ..... A61F 2/4425 623/17.13
2004/0024407 A1 2/2004 Ralph

(56) References Cited

U.S. PATENT DOCUMENTS

2004/0024410 A1 2/2004 Olson et al.
2004/0030391 A1 2/2004 Ferree
2004/0034426 A1 2/2004 Errico et al.
2004/0054411 A1 3/2004 Kelly et al.
2004/0059318 A1 3/2004 Zhang et al.
2004/0073307 A1 4/2004 Keller
2004/0073311 A1 4/2004 Ferree
2004/0073312 A1 4/2004 Eisermann et al.
2004/0093087 A1 5/2004 Ferree et al.
2004/0097928 A1 5/2004 Zdeblick et al.
2004/0098131 A1 5/2004 Bryan et al.
2004/0117021 A1 6/2004 Biedermann et al.
2004/0143270 A1 7/2004 Zucherman et al.
2004/0143332 A1 7/2004 Krueger et al.
2004/0143334 A1 7/2004 Ferree
2004/0167626 A1 8/2004 Geremakis et al.
2004/0176843 A1 9/2004 Zubok et al.
2004/0186569 A1 9/2004 Berry
2004/0215342 A1 10/2004 Suddaby
2004/0225295 A1 11/2004 Zubok et al.
2004/0225365 A1 11/2004 Eisermann et al.
2004/0230307 A1 11/2004 Eisermann et al.
2004/0236426 A1 11/2004 Ralph et al.
2004/0243238 A1 12/2004 Arin et al.
2004/0254644 A1 12/2004 Taylor
2005/0015094 A1 1/2005 Keller
2005/0015095 A1 1/2005 Keller
2005/0015152 A1 1/2005 Sweeney
2005/0021145 A1 1/2005 de Villiers et al.
2005/0021146 A1 1/2005 de Villiers et al.
2005/0027360 A1 2/2005 Webb et al.
2005/0038515 A1 2/2005 Kunzler
2005/0043800 A1 2/2005 Paul et al.
2005/0085917 A1 4/2005 Marnay et al.
2005/0107881 A1 5/2005 Alleyne et al.
2005/0113842 A1 5/2005 Bertagnoli et al.
2005/0113928 A1 5/2005 Cragg
2005/0143824 A1 6/2005 Richelsoph et al.
2005/0149189 A1 7/2005 Mokhtar et al.
2005/0154463 A1 7/2005 Trieu
2005/0165408 A1 7/2005 Puno et al.
2005/0171604 A1 8/2005 Michalow
2005/0187634 A1* 8/2005 Berry ..... 623/17.15
2005/0192586 A1 9/2005 Zucherman et al.
2005/0192670 A1 9/2005 Zubok et al.
2005/0197706 A1 9/2005 Hovorka et al.
2005/0216081 A1 9/2005 Taylor
2005/0216084 A1 9/2005 Fleischmann et al.
2005/0234553 A1 10/2005 Gordon
2005/0251260 A1 11/2005 Gerber et al.
2005/0251261 A1 11/2005 Peterman
2005/0261772 A1 11/2005 Filippi et al.
2005/0267580 A1 12/2005 Suddaby
2005/0267581 A1 12/2005 Marnay et al.
2006/0004377 A1 1/2006 Keller
2006/0004453 A1 1/2006 Bartish et al.
2006/0015183 A1 1/2006 Gilbert et al.
2006/0020342 A1 1/2006 Ferree et al.
2006/0025862 A1 2/2006 Villiers et al.
2006/0030862 A1 2/2006 de Villiers et al.
2006/0036325 A1 2/2006 Paul et al.
2006/0041313 A1 2/2006 Allard et al.
2006/0041314 A1 2/2006 Millard
2006/0052870 A1 3/2006 Feree
2006/0064169 A1 3/2006 Feree et al.
2006/0069439 A1 3/2006 Zucherman et al.
2006/0116768 A1 6/2006 Krueger et al.
2006/0136061 A1 6/2006 Navarro et al.
2006/0142858 A1 6/2006 Colleran
2006/0142862 A1 6/2006 Diaz et al.
2006/0155378 A1 7/2006 Eckman
2006/0167549 A1 7/2006 Mathys et al.
2006/0178744 A1 8/2006 de Villiers et al.
2006/0178746 A1 8/2006 Bartish, Jr. et al.
2006/0195097 A1 8/2006 Evans et al.
2006/0200239 A1 9/2006 Rothman et al.
2006/0200240 A1 9/2006 Rothman et al.
2006/0200242 A1 9/2006 Rothman et al.
2006/0200243 A1* 9/2006 Rothman ..... A61F 2/442 623/17.13
2006/0224241 A1* 10/2006 Butler et al. ..... 623/17.15
2006/0235426 A1 10/2006 Lim et al.
2006/0235525 A1 10/2006 Gil et al.
2006/0235527 A1 10/2006 Buettner-Janz et al.
2006/0241641 A1 10/2006 Albans et al.
2006/0241766 A1 10/2006 Felton et al.
2006/0259144 A1 11/2006 Trieu
2006/0259146 A1 11/2006 Navarro et al.
2006/0265068 A1 11/2006 Schwab
2006/0265077 A1 11/2006 Zwirkoski
2006/0276902 A1 12/2006 Zipnick et al.
2006/0287728 A1 12/2006 Mokhtar et al.
2006/0293752 A1 12/2006 Moumene et al.
2006/0293753 A1 12/2006 Thramann
2006/0293754 A1 12/2006 de Villiers et al.
2007/0010826 A1 1/2007 Rhoda et al.
2007/0021837 A1 1/2007 Ashman et al.
2007/0032875 A1 2/2007 Blacklock et al.
2007/0067035 A1 3/2007 Falahee
2007/0067036 A1 3/2007 Hudgins et al.
2007/0073398 A1 3/2007 Fabian et al.
2007/0093898 A1 4/2007 Schwab et al.
2007/0100453 A1 5/2007 Parsons et al.
2007/0100454 A1 5/2007 Burgess et al.
2007/0100456 A1 5/2007 Dooris et al.
2007/0123903 A1 5/2007 Raymond et al.
2007/0123904 A1 5/2007 Stad et al.
2007/0135923 A1 6/2007 Peterman et al.
2007/0162133 A1 7/2007 Doubler et al.
2007/0168033 A1 7/2007 Kim et al.
2007/0168036 A1 7/2007 Ainsworth et al.
2007/0179615 A1 8/2007 Heinz et al.
2007/0213821 A1 9/2007 Kwak et al.
2007/0233077 A1 10/2007 Khalili
2007/0233247 A1 10/2007 Schwab
2007/0233248 A1 10/2007 Schwab et al.
2007/0233251 A1 10/2007 Abdou
2007/0270956 A1 11/2007 Heinz
2007/0270970 A1 11/2007 Trieu
2007/0282449 A1 12/2007 de Villiers et al.
2007/0299521 A1 12/2007 Glenn et al.
2008/0015698 A1 1/2008 Marino et al.
2008/0015701 A1 1/2008 Garcia et al.
2008/0021557 A1 1/2008 Trieu
2008/0051900 A1 2/2008 de Villiers et al.
2008/0051901 A1 2/2008 de Villiers et al.
2008/0125864 A1 5/2008 de Villiers et al.
2008/0125865 A1 5/2008 Abdelgany
2008/0133011 A1 6/2008 de Villiers et al.
2008/0154301 A1 6/2008 de Villiers et al.
2008/0154305 A1 6/2008 Foley et al.
2008/0154382 A1 6/2008 de Villiers et al.
2008/0161926 A1* 7/2008 Melkent et al. ..... 623/17.16
2008/0215155 A1 9/2008 de Villiers et al.
2008/0221696 A1 9/2008 de Villiers et al.
2008/0228274 A1 9/2008 de Villiers et al.
2008/0228277 A1 9/2008 de Villiers et al.
2008/0294259 A1 11/2008 de Villiers et al.
2009/0043391 A1 2/2009 de Villiers et al.
2009/0048674 A1 2/2009 Zubok et al.
2009/0048677 A1 2/2009 McLeod et al.
2009/0076614 A1 3/2009 Arramon ..... A61F 2/4425 623/17.16
2009/0105833 A1 4/2009 Hovda et al.
2009/0105834 A1 4/2009 Hovda et al.
2009/0105835 A1 4/2009 Hovda et al.
2009/0118836 A1* 5/2009 Cordaro ..... A61F 2/4455 623/17.16
2009/0192617 A1 7/2009 Arramon et al.
2009/0205188 A1 8/2009 de Villiers et al.
2009/0210060 A1 8/2009 de Villiers et al.
2009/0222101 A1 9/2009 de Villiers et al.
2009/0276051 A1 11/2009 Arramon et al.
2009/0326656 A1 12/2009 de Villiers et al.

(56) References Cited

U.S. PATENT DOCUMENTS

| | | | | |
|---|---|---|---|---|
| 2010/0004746 | A1 | 1/2010 | Arramon | |
| 2010/0004748 | A1* | 1/2010 | Cordaro | A61F 2/442 623/17.16 |
| 2010/0016972 | A1 | 1/2010 | Jansen et al. | |
| 2010/0016973 | A1 | 1/2010 | de Villiers et al. | |
| 2010/0030335 | A1 | 2/2010 | Arramon | |
| 2010/0049040 | A1 | 2/2010 | de Villiers et al. | |
| 2010/0069976 | A1 | 3/2010 | de Villiers et al. | |
| 2010/0076558 | A1 | 3/2010 | de Villiers et al. | |
| 2010/0087868 | A1 | 4/2010 | Barr et al. | |
| 2010/0100141 | A1 | 4/2010 | de Villiers et al. | |
| 2010/0179419 | A1 | 7/2010 | de Villiers et al. | |
| 2010/0268344 | A1 | 10/2010 | de Villiers et al. | |
| 2017/0071757 | A1 | 3/2017 | Hovda et al. | |

FOREIGN PATENT DOCUMENTS

| | | | |
|---|---|---|---|
| DE | 10035182 | A1 | 2/2002 |
| EP | 0333990 | A2 | 9/1989 |
| EP | 0333990 | A3 | 5/1990 |
| EP | 0560140 | A1 | 9/1993 |
| EP | 0560141 | A1 | 9/1993 |
| EP | 0591712 | A1 | 4/1994 |
| EP | 0820740 | A1 | 1/1998 |
| EP | 1142544 | A1 | 10/2001 |
| EP | 1153582 | A2 | 11/2001 |
| EP | 1153582 | A3 | 11/2001 |
| EP | 1250898 | A1 | 10/2002 |
| EP | 1306064 | A1 | 5/2003 |
| EP | 1344493 | A1 | 9/2003 |
| EP | 1344506 | A1 | 9/2003 |
| EP | 1344507 | A1 | 9/2003 |
| EP | 1344508 | A1 | 9/2003 |
| EP | 1417940 | A1 | 5/2004 |
| EP | 1570813 | A1 | 9/2005 |
| FR | 2803741 | A1 | 7/2001 |
| JP | 61122859 | A | 6/1986 |
| JP | S61122859 | A | 6/1986 |
| JP | 63164948 | A | 7/1988 |
| JP | S63164948 | A | 7/1988 |
| WO | WO-9920209 | A1 | 4/1999 |
| WO | WO-9930651 | A1 | 6/1999 |
| WO | WO-0004851 | A1 | 2/2000 |
| WO | WO-0035384 | A1 | 6/2000 |
| WO | WO-0042954 | A2 | 7/2000 |
| WO | WO-0042954 | A3 | 11/2000 |
| WO | WO-0101893 | A1 | 1/2001 |
| WO | WO-0115637 | A1 | 3/2001 |
| WO | WO-0168003 | A1 | 9/2001 |
| WO | WO-0211650 | A2 | 2/2002 |
| WO | WO-0211650 | A3 | 9/2003 |
| WO | WO-2004000170 | A1 | 12/2003 |
| WO | WO-2004000171 | A1 | 12/2003 |
| WO | WO-2004026187 | A1 | 4/2004 |
| WO | WO-2004054477 | A1 | 7/2004 |
| WO | WO-2005004756 | A2 | 1/2005 |
| WO | WO-2005004756 | A3 | 5/2005 |
| WO | WO-2005053580 | A1 | 6/2005 |
| WO | WO-2005072662 | A1 | 8/2005 |
| WO | WO-2005112834 | A2 | 12/2005 |
| WO | WO-2005112834 | A3 | 5/2006 |
| WO | WO-2006119092 | A2 | 11/2006 |
| WO | WO-2006119092 | A3 | 12/2006 |
| WO | WO-2007121320 | A2 | 10/2007 |
| WO | WO-2007121320 | A3 | 6/2008 |
| ZA | 2003/9312 | | 11/2003 |
| ZA | 200603171 | | 9/2007 |

OTHER PUBLICATIONS

Office action dated Feb. 8, 2012 for U.S. Appl. No. 12/255,731.
Office action dated Apr. 18, 2012 for U.S. Appl. No. 12/255,733.
Office action dated Jun. 7, 2011 for U.S. Appl. No. 12/255,731.
Office action dated Aug. 26, 2011 for U.S. Appl. No. 12/255,733.
Office action dated Nov. 23, 2012 for U.S. Appl. No. 12/255,731.
Office action dated Nov. 28, 2012 for U.S. Appl. No. 12/255,733.
"ffice Action dated Dec. 19, 2017 for U.S. Appl. No. 15/359,298".
International search report and written opinion dated Dec. 16, 2008 for PCT/US2008/080800.
Office action dated May 13, 2011 for U.S. Appl. No. 12/255,737.
Office action dated Jun. 19, 2012 for U.S. Appl. No. 12/255,737.
Office action dated Dec. 15, 2011 for U.S. Appl. No. 12/255,737.
Office action dated Dec. 18, 2012 for U.S. Appl. No. 12/255,737.
International Search Report and Written Opinion of PCT Application No. PCT/US08/80800, dated Dec. 16, 2008, 11 pages total.
Buttner-Janz, The Development of.the Artificial Disc. Introduction, pp. 1-18, Library of Congress Catalogue No. 92-75582, ISBN 0-9635430-0-8 (1989).
Hellier, et al. Wear Studies for Development of an Intervertebral Disc Prosthesis. Spine, vol. 17 No. 6 Supplement pp. 86-96 (1992).
International search report and written opinion dated Dec. 19, 2008 for PCT/US2008/080798.
International search report and written opinion dated Dec. 29, 2008 for PCT/US2008/080804.
Lee, et al. Impact Response of the Intervertebral Disc in a Finite-Element Model. Spine. 2000; 25(19):2431-2439.
Lehuec, et al. Shock Absorption in Lumber Disc Prosthesis. Journal of Spinal Disorders & Techniques. 2003; 16(4):346-351.
Office action dated Aug. 14, 2013 for U.S. Appl. No. 12/255,731.

* cited by examiner

VERTEBRAL BODY PLACEMENT AND METHOD FOR SPANNING A SPACE FORMED UPON REMOVAL OF A VERTEBRAL BODY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCES TO RELATED APPLICATIONS

This application claims priority under 35 U.S.C. §119 to U.S. Provisional Application No. 60/981,665 filed Oct. 22, 2007, entitled "Method and Spacer Device Spanning Space Formed Upon Removal of an Intervertebral Disc," the full disclosure of which is incorporated herein by reference.

BACKGROUND OF THE INVENTION

The present invention relates to medical devices and methods. More specifically, the invention relates to vertebral body replacements and methods of spanning a space formed upon removal of an intervertebral disc.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Another form of spinal injury involves injury or deformity of the vertebra themselves. When one or more vertebrae is fracture or deformed by tumor or other causes and results in pain and discomfort, surgery is often required. Traditionally, surgical procedures for vertebral replacement have involved removal of the vertebra and fusion of the two vertebrae above and below the missing vertebra. It is necessary to replace the removed vertebra to maintain spacing of adjacent vertebrae. Oftentimes, pins, rods, screws, cages and/or the like are inserted between the vertebrae to act as support structures to hold the vertebrae and graft material in place while they permanently fuse together. These vertebral body replacement procedures generally focus on rigidly fusing the adjacent vertebrae and preventing motion.

However, it would be desirable to achieve immobilization of the vertebrae adjacent a removed vertebral body and maintain spacing between the adjacent vertebrae without the complete rigidity of traditional interbody fusion.

Another problem associated with the typical vertebral body replacement procedure is the subsidence of the cage into the vertebral body. The typical vertebral body replacement cage is formed with a large percentage of open space to allow the bone to grow through and form the bridging bone which immobilizes the vertebrae. However, the large amount of open space means that the load on each segment of the cage is significantly higher than if the cage surface area was larger. This results in the cage subsiding or sinking into the bone over time and allows the space between the vertebrae to collapse.

Therefore, a need exists for improved vertebral body replacement and method for spanning a space and maintaining spacing between two vertebrae after removal of an intervertebral body. Such improved method and intervertebral body replacement would avoid the need for growth of bridging bone between the remaining vertebrae.

BRIEF SUMMARY OF THE INVENTION

Embodiments of the present invention provide a vertebral body replacement with compliance or shock absorption and methods of spanning a space formed upon removal of vertebral body.

In accordance with one of numerous aspects of the present invention, a vertebral body replacement for replacing at least one vertebral body between remaining upper and lower vertebral bodies, the vertebral body replacement comprises a first end plate having an upper surface configured to engage against a surface of the upper remaining vertebral body, and a lower surface opposite the upper surface spanning the first end plate, a second end plate having a lower surface configured to engage against a surface of the lower remaining vertebral body, and a compliant connector section between the first end plate lower surface and the second end plate lower surface, the compliant connector section comprising at least one helical cut configured and arranged to permit limited motion between the first end plate and the second end plate.

In accordance with another aspect of the invention, a method of replacing at least one vertebral body comprises removing said at least one vertebral body between two remaining vertebral bodies, placing a vertebral body replacement between said two remaining vertebral bodies, the vertebral body replacement comprising first and second end plates and a compliant connector section between the first and second end plates, the compliant connector section having at least one helical cut and configured and arranged to limit motion to less than 10 degrees between said remaining vertebral bodies, and maintaining the space between the two remaining vertebral bodies with the vertebral body replacement.

DETAILED DESCRIPTION OF THE INVENTION

Various embodiments of the present invention generally provide for a vertebral body replacement having upper and lower plates or surfaces connected by a central connector portion which provides some limited amount of axial compliance and/or rotational motion between the upper and lower plates or surfaces. The compliant vertebral body replacement according to the present invention can maintain disc height and prevent subsidence with a large surface area while improving outcomes by allowing some limited motion and providing improved fixation. The compliance of the vertebral body replacement also functions to reduce loading on the interface between the bone and vertebral body replacement.

Figure 1:
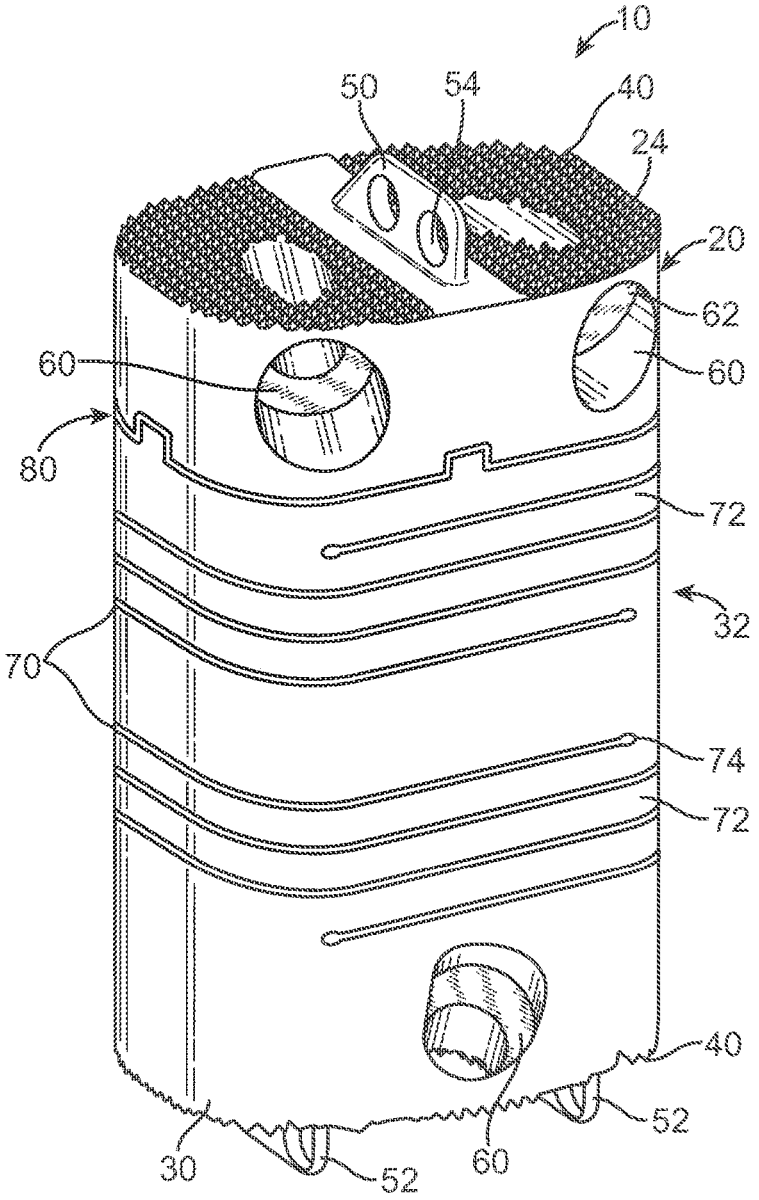
FIG. 1 is a perspective view of a vertebral body replacement according to one embodiment of the present invention.

One example of a vertebral body replacement 10 for replacement of a vertebral body and maintaining disc height between two adjacent vertebral discs is shown in FIG. 1. The body 10 includes at least one end plate 20 having a vertebral body contacting surface 24, a second end plate or body end 30 opposite the end plate 20, and a compliant connector or connector section 32 interposed between, or interconnecting, the two ends 20, 30. As will be described below, some limited rotational and axial motion may be provided between the two plates or sections 20, 30 to reduce loading on the interface between the adjacent vertebral bodies and the body 10. According to an exemplary device embodying principles of the present invention, the compliance of the connector 32, as well as some small amount of translation and rotation, is provided by lateral cuts or slots 70 extending into the connector 32. The body 10 when implanted between two vertebrae maintains a desirable space between the two adjacent vertebrae similar to that provided by a natural vertebra.

Although the body 10 has been shown as generally oblong in cross section, other shapes may be used, including circular, oval, elliptical, or rectangular. Although the connector section 32 has been illustrated in FIG. 1 as integral with the end section 30, according to other embodiments, the connector can include one or more separate compliant connectors or spacers in other configurations and at other locations. By way of example, a compliant connector may be the same or substantially the same diameter, size, and shape as the plates, multiple connectors can be arranged in a rectangular pattern, or a hollow cylindrical connector can be used. Further optionally, while the surfaces 24 are illustrated being perpendicular to the vertical axis of the body 10, one or both of the surfaces 24 can be somewhat wedge-shaped, formed with one or two lordosis angles, as well known to those of ordinary skill in the art. The modular design of the upper plate 20 and the lower plate section 30 allows the creation of a complete bodies 10 of different sizes to correspond to the particular space for each patient.

The upper plate 20 and the lower plate or plate section 30, and connector 32, may be constructed from any suitable metal, alloy or combination of metals or alloys, such as but not limited to cobalt chrome alloys, titanium (such as grade 5 titanium), titanium based alloys, tantalum, nickel titanium alloys, stainless steel, and/or the like. They may also be formed of ceramics, biologically compatible polymers including PEEK, UHMWPE (ultra high molecular weight polyethylene) or fiber reinforced polymers. However, when polymer is used for the body 10, the contacting surfaces 24 may be coated or otherwise covered with metal for fixation. The upper plate 20 and the lower plate or plate section 30, and connector 32, may be formed of a one piece construction or may be formed of more than one piece, such as different materials coupled together. When the body 10 is formed of multiple materials, these materials are fixed together to form a unitary one piece spacer without separately moving parts.

Different materials may be used for different parts of the body 10 to optimize imaging characteristics. For example, the upper plate 20 and the lower plate or plate section 30 may be formed of titanium, while the connector 32 is formed of cobalt chromium alloy for improved imaging of the plates. Cobalt chrome molybdenum alloys, when used for the plates 20, 30 may be treated with aluminum oxide blasting followed by a titanium plasma spray to improve bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof. Any suitable technique may be used to couple materials together, such as snap fitting, slip fitting, lamination, interference fitting, use of adhesives, welding and/or the like.

In some embodiments, the outer surface 24 is planar. Oftentimes, the outer surface 24 will include one or more surface features and/or materials to enhance attachment of the body 10 to vertebral bone. For example, as shown in FIG. 1, the outer surface 24 may be machined to have serrations 40 or other surface features for promoting adhesion of the plates 20, 30 to a vertebra. In the embodiment shown, the serrations 40 are pyramid shaped serrations extending in mutually orthogonal directions, but other geometries such as teeth, grooves, ridges, pins, barbs or the like would also be useful. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surface 24 may be provided with a rough microfinish formed by blasting with aluminum oxide microparticles or the like to improve bone integration. In some embodiments, the outer surface may also be titanium plasma sprayed or HA coated to further enhance attachment of the outer surface 24 to vertebral bone.

The outer surfaces 24 may also carry one or more upstanding fins 50, 52 which also extend laterally in an anterior-posterior direction. The fins 50, 52 are configured to be placed in slots in the vertebral bodies. Preferably, the fins 50, 52 each have a height greater than a width and have a lateral length greater than the height. In one embodiment, the fins 50, 52 are pierced by transverse holes 54 for bone ingrowth. The transverse holes 54 may be formed in any shape and may extend partially or all the way through the fins 50, 52. In alternative embodiments, the fins 50, 52 may be rotated away from the anterior-posterior axis, such as in a lateral-lateral orientation, a posterolateral-anterolateral orientation, or the like.

The fins 50, 52 provide improved attachment to the bone and prevent rotation of the plates 20, 30 in the bone. In some embodiments, the fins 50, 52 may extend from the surface 24 at an angle other than 90°. For example, on one or more of the plates 20, 22 where multiple fins 52 are attached to the surface 24, the fins may be canted away from one another with the bases slightly closer together than their edges at an angle such as about 80-88 degrees. The fins 50, 52 may have any other suitable configuration including various numbers angles and curvatures, in various embodiments. In some embodiments, the fins 50, 52 may be omitted altogether. The embodiment of FIG. 1 illustrates a combination of one plate with a single fin 50 and another plate with a double fin 52. This arrangement is useful for double level disc replacements and utilizes offset slots in the vertebral body to prevent the rare occurrence of vertebral body splitting by avoiding cuts to the vertebral body in the same plane for multi-level implants. The combination of the single fin 50 and double fin 52 can also assist the surgeon in placement of the spacer in the correct orientation.

The body 10 has been shown with the fins 50, 52 as the primary fixation feature; however, the fins may also be augmented or replaced with one or more screws extending through the plates and into the bone. For example in the body 10 of FIG. 1, the upper fin 50 may be augmented or replaced with one or more screws (not illustrated) while the two lower fins 52 remain. The plates 20, 30 can be provided with one or a series of holes 60 to allow screws to be inserted at different locations at the option of the surgeon. However, the holes 60 should not be of such size or number that the coverage of the plate 20, 30 is decreased to such an extent that subsidence occurs. Alternately, the screws can pass laterally through one or more of the holes in the fins. When one or more screws are provided, they may incorporate a locking feature to prevent the screws from backing out. The screws may also be provided with a bone integration coating.

Some limited holes may also be provided in the plate to allow bone ingrowth. However, if the outer surfaces 24 have holes therein, the holes advantageously cover less than 40 percent of the outer surface 24 which contacts the bone to prevent subsidence of the plates into the vertebral bodies. Preferably the holes will cover less than 25 percent, and more preferably less than 10 percent of the outer bone contacting surfaces. At the option of the surgeon, when the small holes are present in the plates 20, 30, bone graft can be placed in the holes to allow bone to grow through the plates. The embodiments illustrated in FIGS. 1-3 also illustrate the optional inclusion of countersunk screw holes 60 extending between a lateral surface of the plates 20, 30 and the end surfaces 24, in which bone screws may optionally be inserted to further stabilize the body 10. The holes 60 can alternatively extend vertically through the end plates, or the end plates can include combinations of vertical and angled holes.

The vertebral body replacement 10 shown herein is configured for placement in the vertebral column from an anterior approach. It should be understood that other approaches can be used, and the particular shape of the vertebral body replacement would be modified depending on the approach. For example, for a lateral approach, the vertebral body replacement may be formed in a more elongated, kidney bean, or banana shape with a transversely oriented fin.

As shown in FIG. 1, the vertebral body replacement 10 is provided with shock absorption or some other limited motion between the two plates 20, 30 by providing a compliant connector 32. The limited motion provided by the compliant connector 32 is designed to reduce forces on the interface between the outer surfaces 24 and the bone to improve long term fixation of the spacer. The compliance of the connector 32 allows motion between the vertebral bodies to be accommodated by the compliance in the body 10 rather than causing one or both of the vertebral bodies to pull away from the plates 20, 30. The compliant connector 32 provides limited relative motion between the plates, which may include compliance in a vertical direction of up to about 6 mm, rotation in an anterior/posterior direction, lateral direction, or axial rotation of less than about 10 degrees, and/or translation of up to about 1 mm.

In the vertebral body replacement 10 of FIG. 1, the compliance, as well as some small amount of translation and rotation, is provided by the cuts or slots 70 extending into the connector 32. In the embodiment of FIG. 1, the slots 70 are spiral slots, however, other shaped slots may also be used. The compliant connector 32 is advantageously formed as a unitary member with at least one lateral cut or slot 70 positioned between the upper and lower plates 20, 30, permitting the plates to move resiliently toward and away from each other. The replacement 10 can also be formed as multiple parts where different properties are desired from the different parts, such as different radiopacities, different strengths, or different flexibility properties and for flexibility in creating the size and configuration of spacer suited to the patient. The lateral cuts 70 in the connector 32 allow the connector to function as a compliant member without affecting the function of the upper and lower plates of the body 10.

Figure 2:
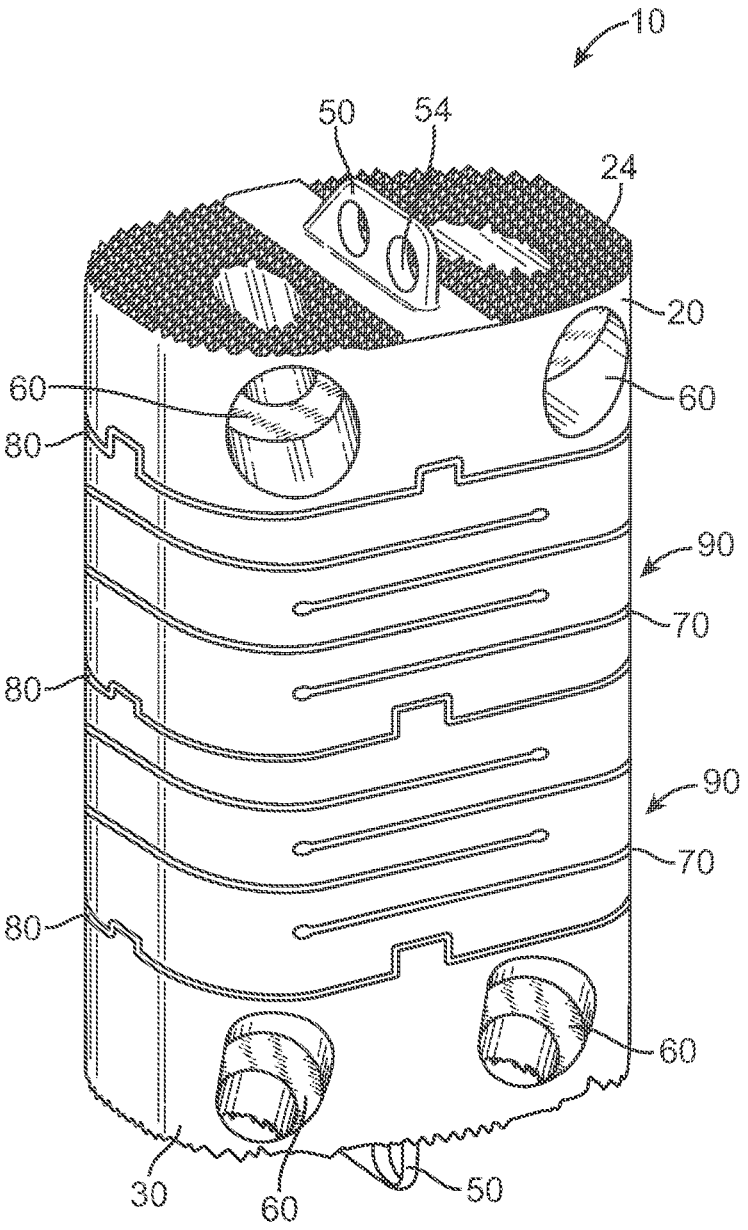
FIG. 2 is a perspective view of a vertebral body replacement according to a second exemplary embodiment of the present invention.

FIG. 2 illustrates an alternative embodiment of a body 10 having multiple parts including end plates 20, 30 and spacers 90. The spacers 90 include lateral cuts 70 in place of the spiral cuts of FIG. 1. The material remaining after the cuts 70 are made is called a column. A shallow cut, that is, one that extends laterally into the connector a relatively small distance, and a large column provides a stiffer spacer, while a deeper cut and smaller column provides a more compliant spacer. In the embodiment shown in FIG. 2, the cuts 70 are at least 60% of the way through the spacer width or diameter, and preferably at least 75% of the way through the connector width.

Optionally, a variable stiffness shock absorbing connector 32 (FIG. 1) or spacer 90 (FIG. 2) can be constructed with lateral cuts 70 with tapering widths. For cuts with such tapering widths, the cut 70 is smallest where the cut terminates adjacent the column and is largest at the edge of the connector 32 furthest from the column. In this version, each of the lateral cuts 70 causes the connector 32 to act as a non linear spring providing progressively stiffer behavior upon larger compression. This is due to the fact that progressively more material on the sides of the cuts 70 is in contact as the connector 32 or spacer 90 is compressed. The non-linear spring can be incorporated in any of the other embodiments described herein to provide a softer stop to the compliant action of the core. The tapered width cuts 70 can provide the additional benefit of providing a flushing action during operation that moves any accumulated material out of the cuts.

The cuts 70 also advantageously include a stress relief 74 at the end of the cuts which increases the fatigue life of the device by reducing the stress concentration at the ends of the slots.

In the exemplary embodiments illustrated herein, a shock absorbing connector 32 includes either one or more planar cuts 70 (FIG. 2), or alternatively one or more spiral or helical cuts 70 (FIG. 1) to form one or more continuous spring coil elements 72 which provide compliance to the connector. Although the spiral cut connector 32 is illustrated in FIG. 1 with two spiral cuts, only one, or three or more spiral cuts may also be employed. For example, two or more spiral cuts 70 arranged in opposite directions can be formed in the connector 32, as illustrated in FIG. 1. Furthermore, when more than one spiral cut 70 is provided, the cuts can optionally be nested one inside the other (not illustrated), as in the manner of a multi-start thread, and/or can include combinations of both nested and adjacent cuts (such as those illustrated in FIGS. 1-2). The compression of a spiral cut connector 70 can result in some small amount of relative rotation between the upper and lower surfaces 20, 30. In cases where it is desirable to eliminate this rotation, a connector 32 having multiple spiral cuts in opposite directions can be used. For example, a connector 32 can be formed with a first spiral cut 70 at a top of the connector in a first direction and a second spiral cut 70 at a bottom of the core in an opposite second direction. The first and second spiral cuts can offset rotation of each other resulting in a non rotating compliant connector. The double spiral embodiment of the connector is also more stable in shear than the single coil. Furthermore, coils 74 provide significantly more surface area between the adjoining surfaces of the cuts 70 than do planar cuts, which can be advantageous to allow limited rotational motion. The spiral cuts 70 can be made parallel to the end surfaces of the body 10 or can be angled, as in a cone shape. When the spiral cuts 70 are angled to form a cone shaped spring the cone shaped surfaces can limit the translational movement of the spring.

In each of the shock absorbing connectors described herein, the interconnected sections within the connector and the plate(s) are designed for minimal or no motion between contacting parts to prevent particulate generation. However, since the plates and connectors are made entirely of hard materials such as metals, some minimal rubbing contact may be accommodated. In the exemplary embodiments illustrated in figures herein, a rotational interlock 80 is provided between the lower surface of the end plate 20 and the adjoining upper surface of the connector section 32 of the end plate 30. With reference to FIG. 2, the exemplary interlock 80 includes complementary portions 82, 84, formed on the adjoining faces of the end plate 20 and the connector section 32, in the exemplary body 10, taking the shape of simple raised portions or ribs 84 which mate with correspondingly sized and shaped recesses 82. The rotational interlock 80 is not limited to the particular shapes or orientations illustrated in the drawing figures, and can take any shape or orientation which resists, and advantageously prevents, the plate 20 and the connector section 32 from rotating relative to each other. The rotational interlock 80 on the top and bottom surface of a spacer 90 can be different to allow the complete body 10 to be assembled only in a particular desired configuration.

Figure 1A:
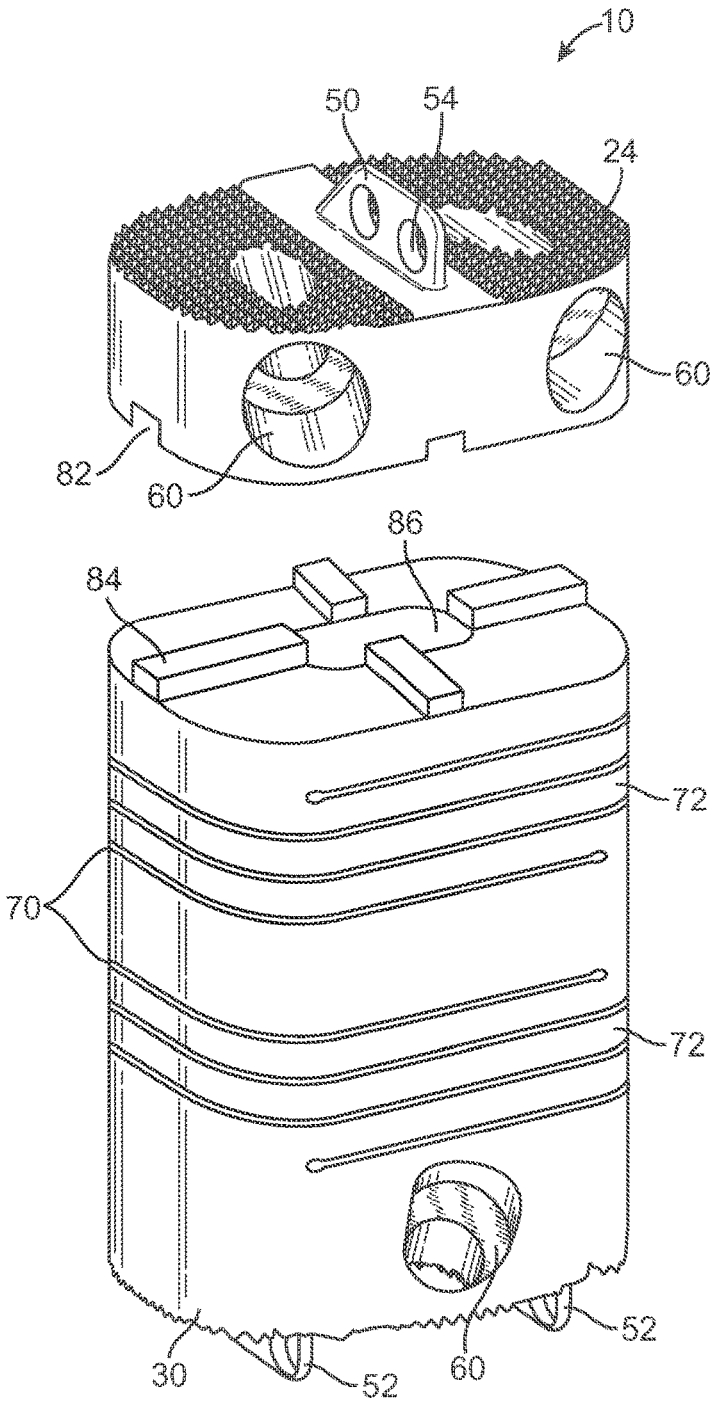
FIG. 1A is an exploded, perspective view of the vertebral body replacement of FIG. 1.

Further optionally, as illustrated in FIG. 1A, the body 10 can include one or more blind cavities 86 extending vertically through the connector section 32, which provides the interior side of the spiral cut 70. The blind cavities 86 can also vary in cross sectional size and shape to tailor the rigidity of the connector section 32 in different directions. More specifically, the cavity or cavities 86, only one of which is illustrated in FIG. 1A, when left hollow, provides a less rigid connector 32. To increase the rigidity of the connector section 32, other material can be used to partially or completely fill the cavity 86, such as pins or rods (not illustrated) inserted in the cavity.

When implanted between vertebrae, the shock absorbing connector 32 can resiliently absorb shocks transmitted vertically between upper and lower vertebrae of the patient's spinal column. This shock absorption is related to the material properties, design, and dimensions of the connector. In general, an increased number and width of the cuts 70 will increase absorption of shocks, with more elastic, or springy compression between the vertebrae.

Preferably the connector 32 is made of metal such as titanium, cobalt chromium alloy, stainless steel, tantalum, nickel titanium or a combination thereof. These materials also can be designed to provide a device which is deformable in the elastic region of the stress/strain curve and will not plastically deform during compression.

In the embodiments illustrated herein, the number, pitch, lead, lead angle, handedness, and total vertical length of each of the spiral cuts or slots 70, as well as the combination of multiple cuts if provided, can be varied to change the amount of compliance of the connector 32. When a load is applied to the upper and lower plates 20, 30, the connector 32 will compress with each of the cuts 70 closing and the total amount of compression possible depending on the number, arrangement, and height of the cuts. The cuts 70 form spiral coils 74 between the ends of the cut, which function like springs to allow the connector 32 to be compressed. The cuts 70 may be modified to be non-uniform to provide preferential deflection in one or more bending directions. Preferential deflection is useful to provide increased anterior-posterior compliance and less lateral compliance, or the other way around.

According to one embodiment of the invention, the cuts 70 in the shock absorbing connector 32 according to any of the embodiments described herein may be manufactured by wire EDM (electrical discharge machining), molding, laser cutting, or the like. A number of cuts 70 can vary from 1 to about 50, preferably about 6 to about 20, for a vertebral body replacement. A width of the lateral cuts 70 in the direction of the height of the body 10 is about 0.01 mm to about 2 mm, preferably about 0.05 to about 1 mm.

In one embodiment of the present invention, for a cervical application, the maximum deformation of the shock absorbing body is about 0.5 to about 4 mm, and is preferably about 1 to about 2 mm. For a lumbar application, the maximum deformation of the shock absorbing body is about 1 to about 6 mm, and is preferably about 1 to about 3 mm.

Although motion between the plates 20, 30 of the body 10 has been described herein as provided by cuts 70, it should be understood that this motion can be provided in a number of other known manners, such as use of resilient materials, or movable joints as long as the motion is limited to the small amount of motion allowable in a patient requiring a fusion procedure including compliance or vertical motion between the plates of up to about 6 mm, rotation between the plates of less than 10 degrees, and translation between the plates of up to about 1 mm.

The body 10 can be provided in different sizes, with different plate sizes, angles between plates, lordosis angles, and heights for different patients or applications. In addition, the shock absorbing connector section 32 can be provided in different compliances for different patients. In addition, the compliance and/or height of the body 10 can be adjustable, such as by rotating an adjustment screw before or after implantation, and/or bonding portions of one or more of the portions of a coil 74. The body 10 preferably is sized to provide substantial coverage of the vertebral surfaces. For example, in an anterior procedure, the plates 20, 30 are preferably sized to cover at least 50 percent of the vertebral surface. In posterior or lateral procedures, the coverage of the vertebral surface may be somewhat smaller due to the small size of the access area, i.e., the posterior or lateral spacers may cover about 40 percent or more of the vertebral surface with a one or two part spacer.

Turning now to FIG. 2, a second exemplary embodiment of a body 10, adhering to principles of the present invention, is illustrated. In contrast to the embodiment illustrated in FIGS. 1 and 1A, the body 10 illustrated in FIG. 2 includes one or more separate compliant connector spacers 90 positioned between plates 20, 30, rather than a connector section 32 of a plate 30. Each of the spacers 90 includes one or more cuts 70, which can be either planar cuts or forming one or more coils, as described above with reference to the embodiment of FIGS. 1 and 1A. The adjoining surfaces of the plates 20, 30 and the spacers 90 are also provided with rotational interlocks 80, as described herein; while FIG. 2 suggests that the interlocks 80 are the same, differently configured interlocks can alternatively be provided for different non-adjoining surfaces, for example to prevent the spacers 90 from being assembled in a way other than that designed for a body 10 configured for the particular patient. By way of non-limiting example, a first rotational interlock, formed of rectangular ribs and recesses on adjoining surfaces of the end plates and/or the spacers, as illustrated in FIG. 1A, can be provided on the adjoining surfaces of the plate 20 and the adjacent first spacer 90; a second rotational interlock, formed of vertically oriented cylindrical pins, can be provided on the opposite face of the first spacer 90 and the adjoining surface of the adjacent spacer or plate 30. Because the two interlocks 80 are incompatible and do not mate, there is only a single configuration of the pieces that will permit them to be assembled into a body 10.

Figure 3:
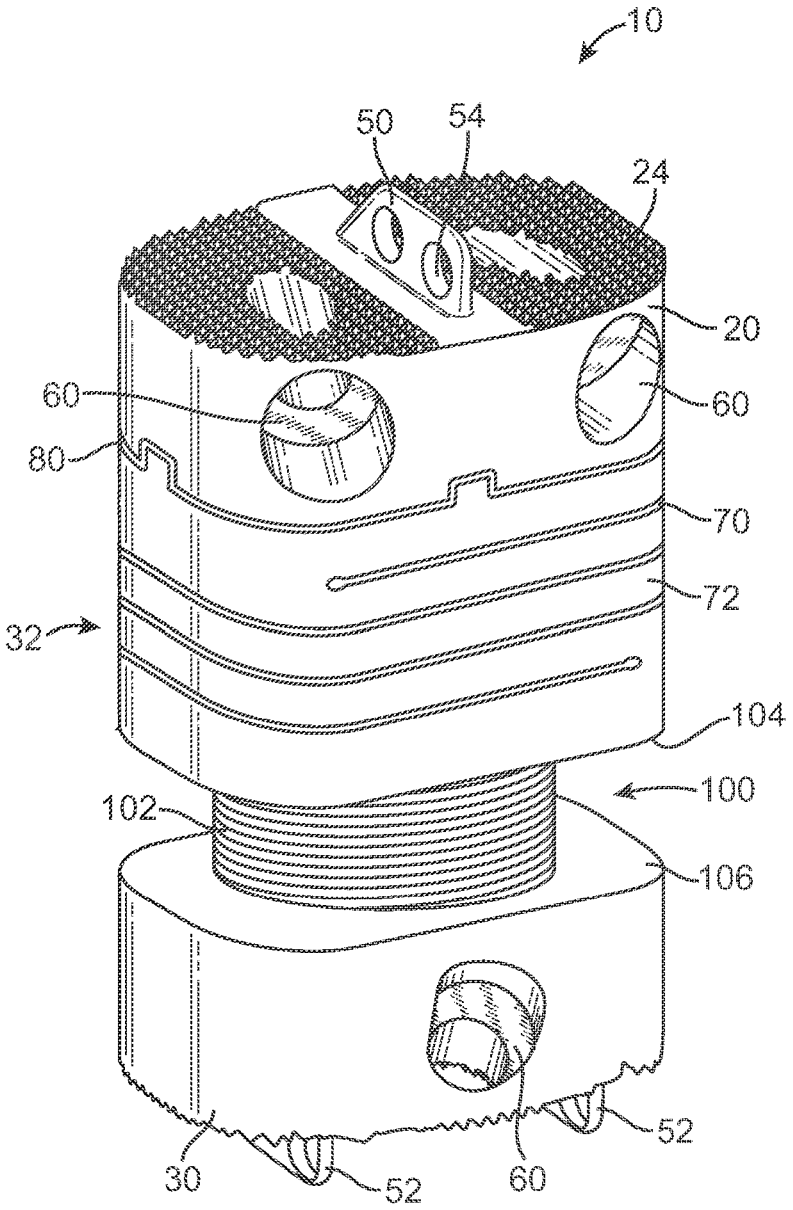
FIG. 3 is a perspective view of a vertebral body replacement according to a third exemplary embodiment of the present invention.

FIG. 3 illustrates a third exemplary embodiment of a body 10, adhering to principles of the present invention. In addition to the features previously described with reference to FIGS. 1-2, the embodiment illustrated in FIG. 3 includes a vertical adjustment mechanism 100 for fine tuning of the vertical size of the body 10, either prior to or after implantation of body 10 into a patient. While numerous configurations of the adjustment mechanism 100 can be provided, one exemplary embodiment includes a threaded post or tube 102 extending from either an upper surface 106 of the end plate 30 or a lower surface 104 of the section 32, which mates with a correspondingly configured and threaded hole or post in the other of the end plate 30 and section 32. Rotation of the post 102 causes the two portions of the body 10 to move toward or away from each other, and thus decreases or increases the vertical size of the body 10, respectively. According to one version of the adjustable height vertebral body replacement an adjustment mechanism with oppositely threaded ends is inserted in the upper and lower parts 104, 106 and is adjustable after positioning in the patient.

According to one exemplary method adhering to principles of the present invention, a patient in need of a vertebral body replacement is prepped and surgical access is made to the particular vertebral body to be removed. Access to the surgical site is generally made anteriorly through the abdominal cavity for a lumbar procedure. One or more target vertebral body or bodies is removed in one of numerous manners known to those of ordinary skill in the art, between upper and lower remaining vertebral bodies in the patient's spine, and a vertebral body replacement 10, embodying principles of the present invention, is selected based on the measurement of the spacing for proper spinal alignment. The vertebral body replacement 10 is assembled and implanted in the space created by removal of the original vertebral body or bodies. Optionally, one or more spacers 90 are assembled into the body 10, prior to installation of the body 10 into the patient, and/or the vertical length of the body 10 is adjusted to better fit in the space. Further optionally, when the body 10 includes one or more cavities 86, additional material is inserted into the cavity, prior to implantation of the body, to tailor the rigidity of the body 10, or for other purposes.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A vertebral body replacement for replacing at least one vertebral body between remaining upper and lower vertebral bodies, the vertebral body replacement comprising:

a first end plate having an upper surface configured to engage against a surface of the upper remaining vertebral body, and a lower surface opposite the upper surface spanning the first end plate;

a second end plate having a lower surface configured to engage against a surface of the lower remaining vertebral body;

a compliant connector section between the first end plate lower surface and the second end plate lower surface, the compliant connector section comprising a plurality of separate stackable spacers each having at least one helical cut configured and arranged to permit limited rotation between the first end plate and the second end plate in an anterior/posterior direction and a lateral direction; and a rotational interlock on the first end plate lower surface and an upper surface of at least one of the spacers, the rotational interlock being configured and arranged to inhibit rotational motion between the first end plate lower surface and the at least one spacer upper surface, wherein the rotational interlock comprises a first raised elongate portion extending in the anterior/posterior direction or the lateral direction on one of the first end plate lower surface or the at least one spacer upper surface and a first complementary elongate recess in the opposite surface.

2. The vertebral body replacement of claim 1, wherein the second end plate includes an upper surface opposite the second end plate lower surface and spanning the second end plate, the compliant connector section located between the second end plate lower and upper surfaces.

3. The vertebral body replacement of claim 2, wherein said rotational interlock is a first rotational interlock, and further comprising a second rotational interlock on the first end plate lower surface and the second end plate upper surface, the second rotational interlock configured and arranged to at least inhibit rotational motion between the first end plate lower surface and the second end plate upper surface.

4. The vertebral body replacement of claim 1, wherein the compliant connector section is configured and arranged to limit motion to less than 10 degrees between said remaining vertebral bodies.

5. The vertebral body replacement of claim 1, wherein the at least one helical cut in each of the separate stackable spacers are oppositely oriented.

6. The vertebral body replacement of claim 1, wherein said rotational interlock is a first rotational interlock, wherein the at least one spacer has a lower surface spanning the at least one spacer, wherein the second end plate has an upper surface spanning the second end plate, and further comprising:

a second rotational interlock on the second end plate upper surface and the at least one spacer lower surface, the second rotational interlock configured and arranged to at least inhibit rotational motion between the second end plate upper surface and the at least one spacer lower surface, wherein the second rotational interlock comprises a second raised elongate portion extending in the anterior/posterior direction or the lateral direction on one of the second end plate upper surface or the at least one spacer lower surface and a second complementary elongate recess in the opposite surface.

7. The vertebral body replacement of claim 6, wherein the first and second rotational interlocks are different.

8. The vertebral body replacement of claim 1, further comprising:

an adjustment mechanism between the first and second end plates, the adjustment mechanism configured and arranged to selectively move the first and second end plates towards and away from each other.

9. The vertebral body replacement of claim 1, further comprising at least one bone ingrowth hole in at least one of the first and second end plates.

10. The vertebral body replacement of claim 1, wherein each of the first and second end plates comprise a lateral surface, and wherein the at least one bone ingrowth hole extends between said lateral surface and said surface configured to engage against a surface of a remaining vertebral body.

11. The vertebral body replacement of claim 1, wherein the vertebral body replacement is sized and shaped to replace one or more entire vertebral bodies of the human spine.

12. A vertebral body replacement for replacing at least one vertebral body between remaining upper and lower vertebral bodies, the vertebral body replacement comprising:

a first end plate having an upper surface configured to engage against a surface of the upper remaining vertebral body, and a lower surface opposite the upper surface spanning the first end plate;

a second end plate having a lower surface configured to engage against a surface of the lower remaining vertebral body;

a compliant connector section between the first end plate lower surface and the second end plate lower surface, the compliant connector section comprising a plurality of separate stackable spacers each having at least one helical cut configured and arranged to form a continuous spring coil element; and a rotational interlock on the first end plate lower surface and an upper surface of at least one of the spacers, the rotational interlock being configured and arranged to inhibit rotational motion between the first end plate lower surface and the at least one spacer upper surface, wherein the rotational interlock comprises a raised elongate portion extending in the anterior/posterior direction or the lateral direction on one of the first end plate lower surface or the at least one spacer upper surface and a complementary elongate recess in the opposite surface.

13. The vertebral body replacement of claim 12, wherein the vertebral body replacement is sized and shaped to replace one or more entire vertebral bodies of the human spine.

14. A vertebral body replacement for replacing at least one vertebral body between remaining upper and lower vertebral bodies, the vertebral body replacement comprising:

a first end plate having an upper surface configured to engage against a surface of the upper remaining vertebral body, and a lower surface opposite the upper surface spanning the first end plate;

a second end plate having a lower surface configured to engage against a surface of the lower remaining vertebral body and an upper surface;

a compliant connector section between the first end plate lower surface and the second end plate lower surface, the compliant connector section comprising a plurality of separate stackable spacers each having at least one helical cut configured and arranged to form a continuous spring coil element; and a rotational interlock on the second end plate upper surface and a lower surface of at least one of the spacers, the rotational interlock being configured and arranged to inhibit rotational motion between the second end plate upper surface and the at least one spacer lower surface, wherein the rotational interlock comprises a raised elongate portion extending in the anterior/posterior direction or the lateral direction on one of the second end plate upper surface or the at least one spacer lower surface and a complementary elongate recess in the opposite surface.

15. The vertebral body replacement of claim 14, wherein the vertebral body replacement is sized and shaped to replace one or more entire vertebral bodies of the human spine.

16. A vertebral body replacement for replacing at least one vertebral body between remaining upper and lower vertebral bodies, the vertebral body replacement comprising:

a first end plate having an upper surface configured to engage against a surface of the upper remaining vertebral body, and a lower surface opposite the upper surface spanning the first end plate;

a second end plate having a lower surface configured to engage against a surface of the lower remaining vertebral body and an upper surface opposite the lower surface and spanning the second end plate;

a compliant connector section between the first end plate lower surface and the second end plate lower surface, the compliant connector section comprising a plurality of separate stackable spacers each having at least one helical cut configured and arranged to permit limited rotation between the first end plate and the second end plate in an anterior/posterior direction and a lateral direction; and a rotational interlock on the second end plate upper surface and a lower surface of at least one of the spacers, the rotational interlock being configured and arranged to inhibit rotational motion between the second end plate upper surface and the at least one spacer lower surface, wherein the rotational interlock comprises a raised elongate portion extending in the anterior/posterior direction or the lateral direction on one of the second end plate upper surface or the at least one spacer lower surface and a complementary elongate recess in the opposite surface.

17. The vertebral body replacement of claim 16, wherein the compliant connector section is located between the second end plate lower and upper surfaces.

18. The vertebral body replacement of claim 16, wherein the compliant connector section is configured and arranged to limit motion to less than 10 degrees between said remaining vertebral bodies.

19. The vertebral body replacement of claim 16, wherein the at least one helical cut in each of the separate stackable spacers are oppositely oriented.

20. The vertebral body replacement of claim 16, wherein said rotational interlock is a first rotational interlock, and further comprising a second rotational interlock on the first end plate lower surface and the second end plate upper surface, the second rotational interlock configured and arranged to at least inhibit rotational motion between the first end plate lower surface and the second end plate upper surface.

21. The vertebral body replacement of claim 16, further comprising:

an adjustment mechanism between the first and second end plates, the adjustment mechanism configured and arranged to selectively move the first and second end plates towards and away from each other.

22. The vertebral body replacement of claim 16, further comprising at least one bone ingrowth hole in at least one of the first and second end plates.

23. The vertebral body replacement of claim 16, wherein each of the first and second end plates comprise a lateral surface, and wherein the at least one bone ingrowth hole extends between said lateral surface and said surface configured to engage against a surface of a remaining vertebral body.

24. The vertebral body replacement of claim 16, wherein the vertebral body replacement is sized and shaped to replace one or more entire vertebral bodies of the human spine.

*25. A vertebral body replacement for replacing at least one vertebral body between remaining upper and lower vertebral bodies, the vertebral body replacement comprising:*

*a first end plate having an upper surface configured to engage against a surface of the upper remaining vertebral body and at least one elongated fin on the upper surface configured to enter a slot cut in the upper remaining vertebral body;*

*a second end plate having a lower surface configured to engage against a surface of the lower remaining vertebral body and at least one elongated fin on the lower surface configured to enter a slot cut in the lower remaining vertebral body;*

*a compliant connector section between the first end plate and the second end plate, the compliant connector section comprising a plurality of separate stackable spacers each having at least one helical cut configured and arranged to permit limited rotation between the first end plate and the second end plate in an anterior/posterior direction and a lateral direction, wherein the compliant connector section is configured and arranged to limit motion to less than 10 degrees between said remaining vertebrae.*

*26. The vertebral body replacement of claim 25, wherein the upper and lower surfaces have less than 10 percent comprising holes.*

*27. The vertebral body replacement of claim 25, further comprising one or more holes in the first and second end plates configured to receive screws extending through the plates and into the bone.*

* * * * *